United States Patent
Wang et al.

(10) Patent No.: US 10,376,512 B1
(45) Date of Patent: Aug. 13, 2019

(54) CRYSTAL OF ANILINE PYRIMIDINE COMPOUND OF TRIFLUOROETHYL SUBSTITUTED INDOLE AND SALT THEREOF

(71) Applicant: CHIA TAI TIANQING PHARMACEUTICAL GROUP CO., LTD., Lianyungang (CN)

(72) Inventors: Lulu Wang, Lianyungang (CN); Jianqiu Tang, Lianyungang (CN); Yizhong Zhu, Lianyungang (CN); Fei Liu, Lianyungang (CN); Yan Zhu, Beijing (CN); Chuanyu Zhang, Beijing (CN); Limin Yang, Beijing (CN)

(73) Assignee: CHIA TAI TIANQING PHARMAEUTICAL GROUP CO., LTD., Lianyungang, Jiangsu Province (CN)

( * ) Notice: Subject to any disclaimer, the term of this patent is extended or adjusted under 35 U.S.C. 154(b) by 0 days.

(21) Appl. No.: 16/059,890

(22) Filed: Aug. 9, 2018

(51) Int. Cl.
*A61K 31/506* (2006.01)
*A61P 35/00* (2006.01)

(52) U.S. Cl.
CPC ............ *A61K 31/506* (2013.01); *A61P 35/00* (2018.01)

(58) Field of Classification Search
CPC ............................ C07D 403/04; A61K 31/506
USPC ........................................................ 514/272
See application file for complete search history.

(56) References Cited

FOREIGN PATENT DOCUMENTS

CN 107973782 A 5/2018
EP 3216786 A1 9/2017

*Primary Examiner* — Kahsay Habte
(74) *Attorney, Agent, or Firm* — Kilpatrick Townsend & Stockton LLP

(57) ABSTRACT

The disclosure relates to a crystal of an aniline pyrimidine compound of trifluoroethyl substituted indole and a salt thereof as an EGFR inhibitor, specifically relates to a crystal of a compound represented by formula I, a crystal of monomethyl sulfonate of the compound represented by formula I or a crystal of dimethyl sulfonate of the compound represented by formula I, and further relates to a method for preparing the crystal, a crystalline composition comprising the crystal, or a pharmaceutical composition comprising the crystal or a crystalline composition thereof, and a medical use thereof.

I

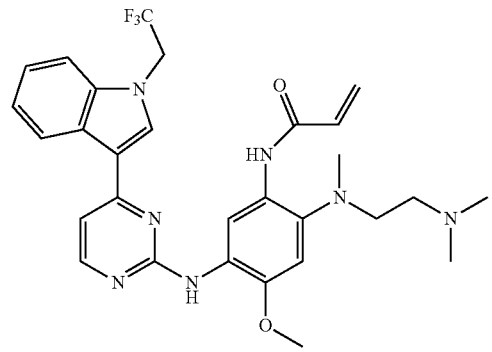

14 Claims, 7 Drawing Sheets

CRYSTAL OF ANILINE PYRIMIDINE COMPOUND OF TRIFLUOROETHYL SUBSTITUTED INDOLE AND SALT THEREOF

TECHNICAL FIELD

The disclosure belongs to the field of pharmaceutical chemistry, and specifically relates to a crystal of an aniline pyrimidine compound (I) of trifluoroethyl substituted indole and a salt thereof.

BACKGROUND

EGFR (epidermal growth factor receptor) is a receptor for cellular proliferation and signal transduction of epithelial growth factors (EGFs), and also known as HER1 or ErbB1. EGFR is one member of ErbB receptor family, which includes EGFR (ErbB-1), HER2/c-neu (ErbB-2), HER3 (ErbB-3), and HER4 (ErbB-4). EGFR is a type of glycoprotein, belongs to a tyrosine kinase receptor, has a transmembrane and a molecular weight of 170 KDa.

EGFR is located on the surface of cell membrane, and is activated by binding to a ligand, including EGF and TGFα. The activated EGFR is converted into a dimer from a monomer. The dimer includes not only a combination of two homologous receptor molecules (homologous dimerization), but also a combination of different members of a human EGF-related receptor (HER) tyrosine kinase family (heterogeneous dimerization). The dimerized EGFR can activate its intracellular kinase pathway, including phosphorylation of key tyrosine residues in the intracellular domain, resulting in stimulation of many intracellular signal transduction pathways involved in the cellular proliferation and survival.

There is high expression or abnormal expression of EGFR in many solid tumors. EGFR is associated with tumor cell proliferation, angiogenesis, tumor invasion, metastasis, and apoptosis inhibition, and the possible mechanisms include: enhancement of downstream signal transduction caused by high expression of EGFR; continuous activation of EGFR caused by increased expression of a mutant EGFR receptor or ligand; enhancement of functions of an autocrine loop; destruction of down regulation mechanism of receptors; activation of an abnormal signal transduction pathway, and the like. Over-expression of EGFR plays an important role in the development of malignant tumors. The over-expression of EGFR has been found in tissues involving gliocyte, kidney cancer, lung cancer, prostate cancer, pancreatic cancer, and breast cancer.

Abnormal expression of EGFR and Erb-B2 plays a key role in the transformation and growth of tumors. Taking the lung cancer as an example, EGFR is expressed in 50% non-small cell lung cancer (NSCLC) cases, and its expression is associated with poor prognosis. The two factors enable EGFR and its family members to become major candidates for targeted therapy. Two small molecule inhibitors targeting EGFR, i.e., gefitinib and erbtinib, have been rapidly approved by the FDA for the treatment of patients with advanced NSCLC, who have lost response to conventional chemotherapy.

Early clinical data show that 10% NSCLC patients have response to gefitinib and erbtinib. Molecular biological analysis shows that in most cases, a patient having response to the drugs has a specific mutation on a gene encoding EGFR: deletion of amino acids 747 to 750 in exon 19 accounts for 45% mutations, and 10% mutations occur in exon 18 and exon 20. The most common EGFR activating mutations (L858R and delE746_A750) lead to increased affinity to the small molecule tyrosine kinase inhibitor (TKI) and decreased affinity to the adenosine triphosphate (ATP), as compared with the wild type (WT) EGFR. T790M mutation is a point mutation in exon 20 of EGFR, and is associated with acquired resistance to gefitinib or erbtinib. A latest research shows that the affinity of the combined L858R and T790M mutation to ATP is stronger than that of L858R only, and TKI is an ATP-competitive kinase inhibitor, thereby resulting in reduced binding rate between TKI and the kinase domain.

Because these mutations play an important role in the drug resistant mechanism of targeting EGFR therapy, it is necessary to provide an EGFR-L858R/T790M double mutation inhibitor for use in clinical treatment. Moreover, because inhibition of EGFR-WT will lead to many clinical toxic and side effects, it is also necessary to provide an inhibitor for use in clinical treatment, which has selectivity for EGFR-activating mutants (such as EGFR-L858R mutants, delE746_A750 mutants or EGFR exon 19 deletion mutants) or resistant EGFR mutants (e.g., EGFR-T790M mutants) as compared with EGFR-WT.

At present, a variety of selective EGFR inhibitors have been reported. WO2016070816 discloses an aniline pyrimidine compound of trifluoroethyl substituted indole:

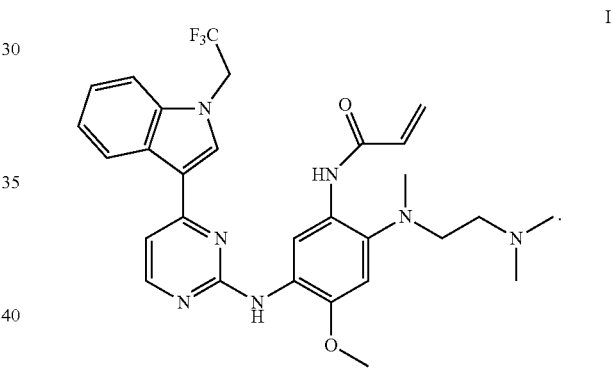

Drug developers try to provide not only therapeutic efficacy, but also appropriate forms of active molecules having a property of forming a drug. Therefore, it is important for drug development to find a form having desired property.

SUMMARY

In an aspect, the disclosure provides a crystal A of a compound represented by formula I, a method for preparing the crystal, a crystalline composition comprising the crystal, or a pharmaceutical composition comprising the crystal or a crystalline composition thereof, and a medical use thereof.

In another aspect, the disclosure provides a crystal B of monomethyl sulfonate of a compound represented by formula I, a method for preparing the crystal, a crystalline composition comprising the crystal, or a pharmaceutical composition comprising the crystal or a crystalline composition thereof, and a medical use thereof.

In yet another aspect, the disclosure provides a crystal C of dimethyl sulfonate of a compound represented by formula I, a crystal D of dimethyl sulfonate of the compound represented by formula I, a crystal E of dimethyl sulfonate of the compound represented by formula I, a crystal F of dimethyl sulfonate of the compound represented by formula I, a crystal G of dimethyl sulfonate of the compound represented by formula I, a method for preparing any one of the crystals, a crystalline composition comprising any one of the crystals, a pharmaceutical composition comprising any one of the crystals or a crystalline composition thereof, and a medical use thereof.

DETAILED DESCRIPTION

In one aspect, the disclosure provides a crystal A of a compound represented by formula I:

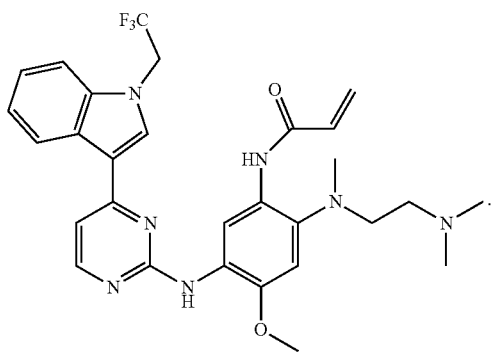

I having diffraction peaks at 2θ=8.58°, 13.10°, 18.32°, 19.39°, and 21.29°±0.2° in an X-ray diffraction (XRD) pattern; typically having diffraction peaks at 2θ=8.58°, 9.98°, 13.10°, 17.53°, 18.32°, 19.39°, and 21.29°±0.2°, and more typically having diffraction peaks at 2θ=8.58°, 9.98°, 13.10°, 17.53°, 18.32°, 19.39°, 20.57°, 21.29°, 23.04°, and 23.76°±0.2°.

In some embodiments of the disclosure, the X-ray diffraction peaks of the crystal A have following characteristics:

| No. | 2θ ± 0.2 (°) | Relative intensity (%) |
|-----|--------------|------------------------|
| 1   | 8.58         | 100                    |
| 2   | 9.98         | 11.4                   |
| 3   | 13.10        | 14.8                   |
| 4   | 14.10        | 6.1                    |
| 5   | 14.87        | 8.4                    |
| 6   | 17.53        | 10.0                   |
| 7   | 18.32        | 33.2                   |
| 8   | 19.39        | 20.3                   |
| 9   | 19.93        | 8.6                    |
| 10  | 20.57        | 13.2                   |
| 11  | 21.29        | 18.2                   |
| 12  | 23.04        | 14.7                   |
| 13  | 23.76        | 13.5                   |
| 14  | 24.80        | 8.0                    |

In some embodiments of the disclosure, the X-ray diffraction pattern of the crystal A according to the disclosure is shown in FIG. 1.

In some embodiments of the disclosure, the DSC thermogram of the crystal A according to the disclosure is shown in FIG. 2.

In another aspect, the disclosure provides a method for preparing the crystal A, comprising:
1) dissolving a compound represented by formula I in a crystallization solvent; and
2) cooling, crystallization, and filtration.

The crystallization solvent is selected from the group consisting of acetonitrile, ethyl acetate, methanol, ethanol, isopropanol, tetrahydrofuran, dioxane, acetone, dichloromethane, and a mixed solvent of any two or more solvents thereof.

In some embodiments of the disclosure, the crystallization solvent is acetonitrile.

In yet another aspect, the disclosure provides a crystalline composition comprising the crystal A. In some embodiments of the disclosure, the crystal A accounts for 50% or more, preferably 80% or more, more preferably 90% or more, and most preferably 95% or more by weight of the crystalline composition.

In still another aspect, the disclosure provides a pharmaceutical composition comprising the crystal A. The pharmaceutical composition comprises a therapeutically effective amount of the crystal A, or a crystalline composition of the crystal A. Furthermore, the pharmaceutical composition may or may not comprise a pharmaceutically acceptable excipient.

In other aspect, the disclosure provides use of the crystal A or a crystalline composition thereof or a pharmaceutical composition thereof in the preparation of a medicine for the treatment of an EGFR-mediated disease.

In one aspect, the disclosure provides a crystal B of monomethyl sulfonate of a compound represented by formula I:

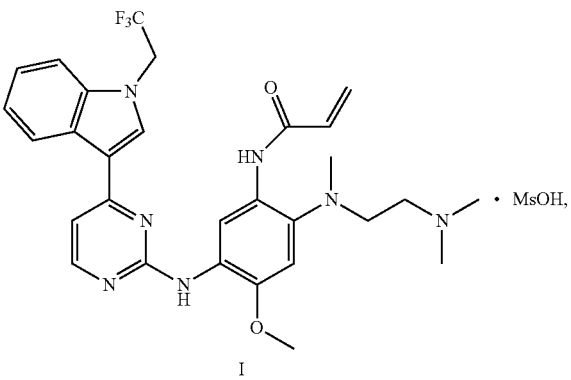

I having diffraction peaks at 2θ=8.05°, 11.08°, 14.17°, 17.98°, 19.20°, 20.78°, and 24.18°±0.2° in an X-ray diffraction (XRD) pattern; typically having diffraction peaks at 2θ=8.05°, 10.46°, 11.08°, 11.48°, 14.17°, 17.98°, 19.20°, 20.78°, 24.18°, and 25.15°±0.2°; more typically having diffraction peaks at 2θ=8.05°, 10.46°, 11.08°, 11.48°, 14.17°, 16.65°, 17.98°, 18.61°, 19.20°, 20.03°, 20.78°, 24.18°, and 25.15°±0.2°; and further typically having diffraction peaks at 2θ=8.05°, 10.46°, 11.08°, 11.48°, 13.86°, 14.17°, 16.65°, 17.98°, 18.61°, 19.20°, 19.40°, 20.03°, 20.78°, 21.12°, 24.18°, 25.15°, and 27.96°±0.2°.

In some embodiments of the disclosure, the X-ray diffraction peaks of the crystal B according to the disclosure have following characteristics:

| No. | 2θ ± 0.2 (°) | Relative intensity (%) |
|-----|--------------|------------------------|
| 1   | 8.05         | 48.3                   |
| 2   | 10.46        | 50.7                   |
| 3   | 11.08        | 56.0                   |
| 4   | 11.48        | 30.8                   |
| 5   | 13.86        | 45.1                   |

| No. | 2θ ± 0.2 (°) | Relative intensity (%) |
|---|---|---|
| 6 | 14.17 | 50.3 |
| 7 | 16.65 | 58.2 |
| 8 | 17.98 | 99.7 |
| 9 | 18.61 | 55.8 |
| 10 | 19.20 | 78.0 |
| 11 | 19.40 | 49.5 |
| 12 | 20.03 | 62.5 |
| 13 | 20.78 | 86.3 |
| 14 | 21.12 | 48.9 |
| 15 | 24.18 | 100.0 |
| 16 | 25.15 | 63.6 |
| 17 | 27.96 | 44.0 |

In some embodiments of the disclosure, the X-ray diffraction pattern of the crystal B according to the disclosure is shown in FIG. 3.

In some embodiments of the disclosure, a DSC thermogram of the crystal B according to the disclosure is shown in FIG. 4.

In another aspect, the disclosure provides a method for preparing the crystal B, comprising:

1) dissolving a compound represented by formula I in a crystallization solvent;

2) adding methanesulfonic acid; and 3) cooling, crystallization, and filtration.

The crystallization solvent is selected from the group consisting of acetonitrile, ethyl acetate, methanol, ethanol, isopropanol, tetrahydrofuran, dioxane, acetone, dichloromethane, water, and a mixed solvent of any two or more solvents thereof; and a ratio of a molar amount of the methanesulfonic acid to a molar amount of the compound represented by formula I is 1:1.

In some embodiments of the disclosure, the crystallization solvent is selected from the group consisting of acetonitrile, ethyl acetate, isopropanol, acetone, dioxane, water and a mixed solvent of any two or more solvents thereof. In some embodiments of the disclosure, the solvent is acetonitrile.

In yet another aspect, the disclosure provides a crystalline composition comprising the crystal B. In some embodiments of the disclosure, the crystal B accounts for 50% or more, preferably 80% or more, more preferably 90% or more, and most preferably 95% or more, by weight of the crystalline composition.

In still another aspect, the disclosure provides a pharmaceutical composition comprising the crystal B. The pharmaceutical composition comprises a therapeutically effective amount of the crystal B, or a crystalline composition of the crystal B. Furthermore, the pharmaceutical composition may or may not comprise a pharmaceutically acceptable excipient.

In other aspect, the disclosure provides use of the crystal B or a crystalline composition thereof or a pharmaceutical composition thereof in the preparation of a medicine for the treatment of an EGFR-mediated disease.

In one aspect, the disclosure provides a crystal C of dimethyl sulfonate of a compound represented by formula I:

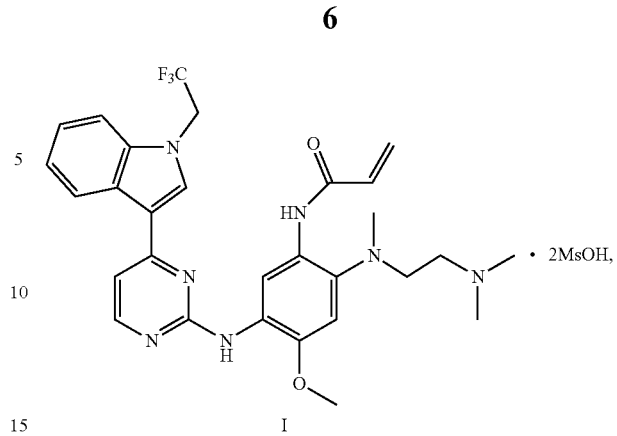

having diffraction peaks at 2θ=6.64°, 8.48°, 17.25°, 20.40°, and 21.87°±0.2° in an X-ray diffraction (XRD) pattern; typically having diffraction peaks at 2θ=6.64°, 8.48°, 13.70°, 15.16°, 17.25°, 20.07°, 20.40°, and 21.87°±0.2°; and more typically having diffraction peaks at 2θ=6.64°, 8.48°, 13.70°, 15.16°, 17.25°, 19.65°, 20.07°, 20.40°, 21.87°, 23.53°, and 25.90°±0.2°.

In some embodiments of the disclosure, the X-ray diffraction peaks of the crystal C according to the disclosure have following characteristics:

| No. | 2θ ± 0.2 (°) | Relative intensity (%) |
|---|---|---|
| 1 | 6.64 | 100.0 |
| 2 | 8.48 | 47.2 |
| 3 | 12.49 | 11.3 |
| 4 | 13.70 | 18.7 |
| 5 | 15.16 | 18.5 |
| 6 | 17.25 | 22.8 |
| 7 | 18.73 | 12.1 |
| 8 | 19.65 | 16.2 |
| 9 | 20.07 | 19.4 |
| 10 | 20.40 | 48.1 |
| 11 | 21.87 | 30.8 |
| 12 | 23.53 | 15.5 |
| 13 | 25.25 | 10.7 |
| 14 | 25.90 | 19.1 |

In some embodiments of the disclosure, the X-ray diffraction pattern of the crystal C according to the disclosure is shown in FIG. 5.

In some embodiments of the disclosure, the DSC thermogram of the crystal C according to the disclosure is shown in FIG. 6.

In another aspect, the disclosure provides a method for preparing the crystal C, comprising:

1) dissolving a compound represented by formula I in a crystallization solvent;

2) adding methanesulfonic acid; and 3) cooling, crystallization, and filtration.

The crystallization solvent is acetonitrile; and a ratio of a molar amount of the methanesulfonic acid to a molar amount of the compound represented by formula I is 2:1.

In yet another aspect, the disclosure provides a crystalline composition comprising the crystal C. In some embodiments of the disclosure, the crystal C accounts for 50% or more, preferably 80% or more, more preferably 90% or more, and most preferably 95% or more, by weight of the crystalline composition.

In still another aspect, the disclosure provides a pharmaceutical composition comprising the crystal C. The pharmaceutical composition comprises a therapeutically effective amount of the crystal C, or a crystalline composition of the crystal C. Furthermore, the pharmaceutical composition may or may not comprise a pharmaceutically acceptable excipient.

In other aspect, the disclosure provides use of the crystal C or a crystalline composition thereof or a pharmaceutical composition thereof in the preparation of a medicine for the treatment of an EGFR-mediated disease.

In one aspect, the disclosure provides a crystal D of dimethyl sulfonate of a compound represented by formula I:

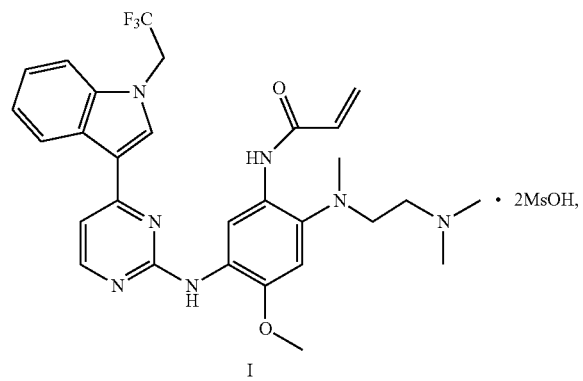

I having diffraction peaks at 2θ=8.04°, 9.35°, 14.42°, 16.23°, 18.64°, 21.83°, and 23.20°±0.2° in an X-ray diffraction (XRD) pattern; typically having diffraction peaks at 2θ=8.04°, 9.35°, 11.86°, 14.42°, 16.23°, 18.64°, 20.32°, 21.83°, 23.30°, and 23.65°±0.2°; more typically having diffraction peaks at 2θ=7.12°, 8.04°, 9.35°, 11.86°, 12.37°, 14.42°, 16.23°, 18.64°, 18.98°, 20.32°, 21.83°, 23.30°, 23.65°, and 24.45°±0.2°; and further typically having diffraction peaks at 2θ=7.12°, 8.04°, 9.35°, 10.37°, 11.86°, 12.37°, 14.42°, 16.23°, 17.79°, 18.64°, 18.98°, 20.32°, 20.82°, 21.83°, 23.30°, 23.65°, 24.22°, and 24.45°±0.2°.

In some embodiments of the disclosure, the X-ray diffraction peaks of the crystal D according to the disclosure have following characteristics:

| No. | 2θ ± 0.2 (°) | Relative intensity (%) |
|---|---|---|
| 1 | 7.12 | 27.7 |
| 2 | 8.04 | 97.5 |
| 3 | 9.35 | 100.0 |
| 4 | 10.37 | 28.0 |
| 5 | 10.80 | 21.5 |
| 6 | 11.86 | 33.2 |
| 7 | 12.37 | 30.5 |
| 8 | 14.42 | 47.8 |
| 9 | 15.08 | 22.3 |
| 10 | 15.91 | 18.3 |
| 11 | 16.23 | 58.3 |
| 12 | 17.79 | 27.3 |
| 13 | 18.64 | 56.4 |
| 14 | 18.98 | 33.1 |
| 15 | 20.32 | 46.3 |
| 16 | 20.82 | 28.3 |
| 17 | 21.83 | 58.6 |
| 18 | 23.30 | 58.2 |
| 19 | 23.65 | 52.5 |
| 20 | 24.22 | 34.4 |
| 21 | 24.45 | 31.9 |
| 22 | 24.80 | 21.8 |
| 23 | 29.60 | 23.5 |

In some embodiments of the disclosure, the X-ray diffraction pattern of the crystal D according to the disclosure is shown in FIG. 7.

In some embodiments of the disclosure, the DSC thermogram of the crystal D according to the disclosure is shown in FIG. 8.

In another aspect, the disclosure provides a method for preparing the crystal D, comprising:

1) dissolving a compound represented by formula I in a crystallization solvent;

2) adding methanesulfonic acid; and 3) cooling, crystallization, and filtration.

The crystallization solvent is ethyl acetate; and a ratio of a molar amount of the methanesulfonic acid to a molar amount of the compound represented by formula I is 2:1.

In yet another aspect, the disclosure provides a crystalline composition comprising the crystal D. In some embodiments of the disclosure, the crystal D accounts for 50% or more, preferably 80% or more, more preferably 90% or more, and most preferably 95% or more, by weight of the crystalline composition.

In still another aspect, the disclosure provides a pharmaceutical composition comprising the crystal D. The pharmaceutical composition comprises a therapeutically effective amount of the crystal D, or a crystalline composition of the crystal D. Furthermore, the pharmaceutical composition may or may not comprise a pharmaceutically acceptable excipient.

In yet another aspect, the disclosure provides use of the crystal D or a crystalline composition thereof or a pharmaceutical composition thereof in the preparation of a medicine for the treatment of an EGFR-mediated disease.

In one aspect, the disclosure provides a crystal E of dimethyl sulfonate of a compound represented by formula I:

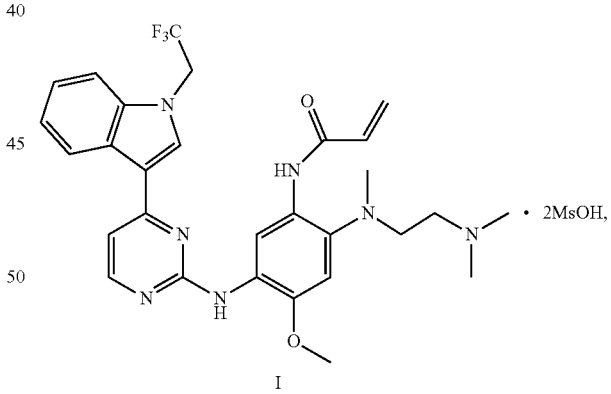

I having diffraction peaks at 2θ=6.98°, 11.85°, 17.83°, 18.76°, 20.29°, 23.26°, and 23.99°±0.2° in an X-ray diffraction (XRD) pattern; typically having diffraction peaks at 2θ=6.98°, 10.98°, 11.85°, 17.00°, 17.83°, 18.76°, 20.29°, 22.84°, 23.26°, and 23.99°±0.2°; and more typically having diffraction peaks at 2θ=6.98°, 10.98°, 11.85°, 12.30°, 17.00°, 17.83°, 18.76°, 20.29°, 21.65°, 22.84°, 23.26°, 23.99°, and 25.69°±0.2°.

In some embodiments of the disclosure, the X-ray diffraction peaks of the crystal E according to the disclosure have following characteristics:

| No. | 2θ ± 0.2 (°) | Relative intensity (%) |
|---|---|---|
| 1 | 6.98 | 100.0 |
| 2 | 10.98 | 17.1 |
| 3 | 11.85 | 54.8 |
| 4 | 12.30 | 22.8 |
| 5 | 13.70 | 16.2 |
| 6 | 14.31 | 10.8 |
| 7 | 15.63 | 13.1 |
| 8 | 17.00 | 28.0 |
| 9 | 17.83 | 42.0 |
| 10 | 18.76 | 36.6 |
| 11 | 19.39 | 14.6 |
| 12 | 20.29 | 28.2 |
| 13 | 21.65 | 31.3 |
| 14 | 22.84 | 36.1 |
| 15 | 23.26 | 54.9 |
| 16 | 23.67 | 18.7 |
| 17 | 23.99 | 47.2 |
| 18 | 24.82 | 17.9 |
| 19 | 25.69 | 23.0 |
| 20 | 27.11 | 19.3 |

In some embodiments of the disclosure, the X-ray diffraction pattern of the crystal E according to the disclosure is shown in FIG. 9.

In some embodiments of the disclosure, the DSC thermogram of the crystal E according to the disclosure is shown in FIG. 10.

In another aspect, the disclosure provides a method for preparing the crystal E, comprising:

1) dissolving a compound represented by formula I in a crystallization solvent;

2) adding methanesulfonic acid; and 3) cooling, crystallization, and filtration.

The crystallization solvent is dichloromethane; and a ratio of a molar amount of the methanesulfonic acid to a molar amount of the compound represented by formula I is 2:1.

In yet another aspect, the disclosure provides a crystalline composition comprising the crystal E. In some embodiments of the disclosure, the crystal E accounts for 50% or more, preferably 80% or more, more preferably 90% or more, and most preferably 95% or more, by weight of the crystalline composition.

In still another aspect, the disclosure provides a pharmaceutical composition comprising the crystal E. The pharmaceutical composition comprises a therapeutically effective amount of the crystal E, or a crystalline composition of the crystal E. Furthermore, the pharmaceutical composition may or may not comprise a pharmaceutically acceptable excipient.

In other aspect, the disclosure provides use of the crystal E or a crystalline composition thereof or a pharmaceutical composition thereof in the preparation of a medicine for the treatment of an EGFR-mediated disease.

In one aspect, the disclosure provides a crystal F of dimethyl sulfonate of a compound represented by formula I:

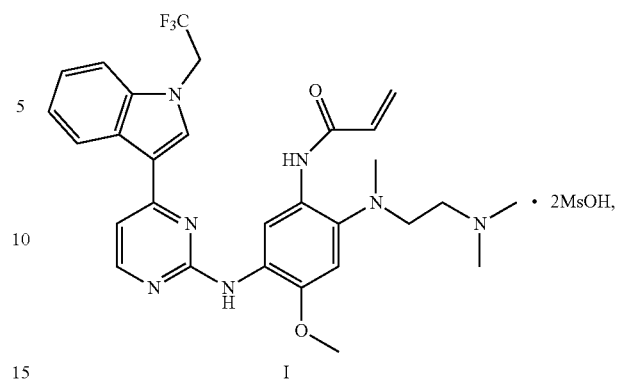

having diffraction peaks at 2θ=6.53°, 7.52°, 11.84°, 19.02°, 19.41°, 20.16°, 23.50°±0.2° in an X-ray diffraction (XRD) pattern; typically having diffraction peaks at 2θ=6.53°, 7.52°, 11.84°, 14.29°, 19.02°, 19.41°, 20.16°, 21.96°, 23.50°, 24.90°, 27.26°±0.2°; and more typically having diffraction peaks at 2θ=6.53°, 7.52°, 11.84°, 13.17°, 14.29°, 15.17°, 18.60°, 19.02°, 19.41°, 20.16°, 21.51°, 21.96°, 23.50°, 24.90°, and 27.26°±0.2°.

In some embodiments of the disclosure, the X-ray diffraction peaks of the crystal F according to the disclosure have following characteristics:

| No. | 2θ ± 0.2 (°) | Relative intensity (%) |
|---|---|---|
| 1 | 6.53 | 49.4 |
| 2 | 7.52 | 64.7 |
| 3 | 11.84 | 60.6 |
| 4 | 13.17 | 31.2 |
| 5 | 14.29 | 39.8 |
| 6 | 15.17 | 36.5 |
| 7 | 17.23 | 19.2 |
| 8 | 18.60 | 29.6 |
| 9 | 19.02 | 100.0 |
| 10 | 19.41 | 41.7 |
| 11 | 20.16 | 83.9 |
| 12 | 21.51 | 27.8 |
| 13 | 21.96 | 37.7 |
| 14 | 23.00 | 21.1 |
| 15 | 23.50 | 57.3 |
| 16 | 24.90 | 34.1 |
| 17 | 26.67 | 17.0 |
| 18 | 27.26 | 26.3 |

In some embodiments of the disclosure, the X-ray diffraction pattern of the crystal F according to the disclosure is shown in FIG. 11.

In some embodiments of the disclosure, the DSC thermogram of the crystal F according to the disclosure is shown in FIG. 12.

In another aspect, the disclosure provides a method for preparing the crystal F, comprising:

1) dissolving a compound represented by formula I in a crystallization solvent;

2) adding methanesulfonic acid; and 3) cooling, crystallization, and filtration.

The crystallization solvent is acetone; and a ratio of a molar amount of the methanesulfonic acid to a molar amount of the compound represented by formula I is 2:1.

In yet another aspect, the disclosure provides a crystalline composition comprising the crystal F. In some embodiments of the disclosure, the crystal F accounts for 50% or more, preferably 80% or more, more preferably 90% or more, and most preferably 95% or more, by weight of the crystalline composition.

In still another aspect, the disclosure provides a pharmaceutical composition comprising the crystal F. The pharmaceutical composition comprises a therapeutically effective amount of the crystal F, or a crystalline composition of the crystal F. Furthermore, the pharmaceutical composition may or may not comprise a pharmaceutically acceptable excipient.

In other aspect, the disclosure provides use of the crystal F or a crystalline composition thereof or a pharmaceutical composition thereof in the preparation of a medicine for the treatment of an EGFR-mediated disease.

In one aspect, the disclosure provides a crystal G of dimethyl sulfonate of a compound represented by formula I:

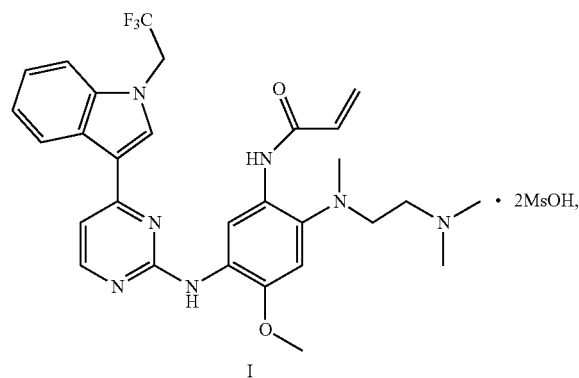

I having diffraction peaks at 2θ=6.80°, 9.71°, 15.11°, 18.35°, 19.91°, and 25.48°±0.2° in an X-ray diffraction (XRD) pattern; typically having diffraction peaks at 2θ=6.80°, 9.71°, 12.32°, 15.11°, 17.64°, 18.35°, 19.91°, 21.26°, 23.60°, and 25.48°±0.2°; and more typically having diffraction peaks at 2θ=6.80°, 9.71°, 12.32°, 13.32°, 15.11°, 17.64°, 18.35°, 18.72°, 19.91°, 21.26°, 23.11°, 23.60°, 24.51°, and 25.48°±0.2°.

In some embodiments of the disclosure, the X-ray diffraction peaks of the crystal G according to the disclosure have following characteristics:

| No. | 2θ ± 0.2 (°) | Relative intensity (%) |
|---|---|---|
| 1 | 6.80 | 95.6 |
| 2 | 9.71 | 77.9 |
| 3 | 12.32 | 36.9 |
| 4 | 12.77 | 21.8 |
| 5 | 13.32 | 29.3 |
| 6 | 15.11 | 49.4 |
| 7 | 17.18 | 23.5 |
| 8 | 17.64 | 44.8 |
| 9 | 18.35 | 51.0 |
| 10 | 18.72 | 39.1 |
| 11 | 19.14 | 26.9 |
| 12 | 19.91 | 68.7 |
| 13 | 21.26 | 44.6 |
| 14 | 22.14 | 43.9 |
| 15 | 23.11 | 35.4 |
| 16 | 23.60 | 47.1 |
| 17 | 24.51 | 33.2 |
| 18 | 25.48 | 100.0 |
| 19 | 26.38 | 34.4 |
| — | — | — |

In some embodiments of the disclosure, the X-ray diffraction pattern of the crystal G according to the disclosure is shown in FIG. 13.

In some embodiments of the disclosure, the DSC thermogram of the crystal G according to the disclosure is shown in FIG. 14.

In another aspect, the disclosure provides a method for preparing the crystal G, comprising:
1) dissolving a compound represented by formula I in a crystallization solvent;
2) adding methanesulfonic acid; and
3) cooling, crystallization, and filtration.

The crystallization solvent is dioxane; and a ratio of a molar amount of the methanesulfonic acid to a molar amount of the compound represented by formula I is 2:1.

In yet another aspect, the disclosure provides a crystalline composition comprising the crystal G. In some embodiments of the disclosure, the crystal G accounts for 50% or more, preferably 80% or more, more preferably 90% or more, and most preferably 95% or more, by weight of the crystalline composition.

In still another aspect, the disclosure provides a pharmaceutical composition comprising the crystal G. The pharmaceutical composition comprises a therapeutically effective amount of the crystal G, or a crystalline composition of the crystal G. Furthermore, the pharmaceutical composition may or may not comprise a pharmaceutically acceptable excipient.

In other aspect, the disclosure provides use of the crystal G or a crystalline composition thereof or a pharmaceutical composition thereof in the preparation of a medicine for the treatment of an EGFR-mediated disease.

In the disclosure, the X-ray diffraction patterns are obtained according to the followings: instrument: Bruker D2X-ray diffractometer; method: target: Cu; tube voltage: 30 kV; tube current: 10 mA; scan range: 4-40°; scanning speed: 0.1 sec/step, 0.02°/step.

In the disclosure, the differential scanning calorimetry (DSC) is obtained according to followings: instrument: Mettler DSC-1 differential scanning calorimeter; method: samples (about 5 mg) are tested in an aluminum pan for DSC; method: 30° C.-300° C., and a heating rate of 10° C./min.

In the disclosure, a ratio of a molar amount of the compound represented by formula I to a molar amount of the acid radical ion that forms salt can be detected by ion chromatography with reference to the measurement method: instrument: DIONEX ICS-2100 ion chromatograph; detector: DIONEX electrical conductivity detector; work station: Chromeleon 7.2; chromatographic column: DIONEX RFI-C™Ionpac® AS11-HC (4×250 mm); mobile phase: 10 mmol of potassium hydroxide eluent; flow rate: 1.0 mL/min; detection current: 25 mA; column temperature: 30° C.; method: an appropriate amount of the product is accurately weighed, dissolved in ultrapure water, and diluted to a solution comprising about 40 μg of the product per mL, which is fully shaken for use as a test solution. An appropriate amount of methanesulfonic acid is accurately weighed, diluted with ultrapure water to a solution comprising about 10 μg of methanesulfonic acid per mL for use as a control solution. 10 μL of the control solution and 10 μL of the test solution are precisely measured, and injected into an ion chromatograph instrument to record the chromatogram. The peak area is calculated according to the external standard method.

It should be noted that, in an X-ray diffraction spectrum, a diffraction pattern obtained from a crystal compound is often characteristic for a specific crystal form, in which the relative intensities of spectral bands (especially at low angles) may vary with the dominant orientation effect caused by the difference in crystallization condition, particle size, and other measurement conditions. Thus, relative intensities of the diffraction peaks are not characteristic for the targeted crystal forms, and when determining whether the targeted crystal form is identical to a known crystal form, more attention should be paid to relative position of the peaks, rather than the relative intensities thereof. In addition, for any given crystal form, the peak position may have a slight error, which is also well known in the field of crystallography. For example, due to the temperature change, sample moving, instrument calibration or the like during the sample analysis, the peak position may move, and the measurement error of the 2θ value is sometimes about ±0.2°. Therefore, the structure of each crystal form should be determined after considering this error. 2θ angle or an interplanar distance d is often used to express a peak position in an XRD pattern, there is a simple conversion relationship therebetween: $d=\lambda/2 \sin \theta$, wherein d represents an interplanar distance, λ, represents a wavelength of an incident X-ray, and θ is a diffraction angle. For the same type of crystal form of a compound, the peak position of the XRD pattern has a similarity on the whole, but the relative intensity errors may be large. It should also be noted that, in the identification of a mixture, deletion of some diffracted rays will be caused by content decrease or other factors. In this case, it is not necessary to rely on all spectral bands observed in a high-purity sample, or even one spectral band may be characteristic for a given crystal.

It should be noted that DSC measures a transition temperature when a crystal is absorbing or releasing heat due to the crystal structure change or the crystal melting. For the same type of crystal form of a compound, during continuous analysis, the thermal transition temperature and the melting point error are typically within about 5° C. When a compound is said to have a given DSC peak or melting point, it means the DSC peak or melting point ±5° C. DSC provides an auxiliary method for distinguishing different crystal forms. Different crystal forms may be identified according to different transition temperature characteristics thereof.

In the disclosure, the term "pharmaceutical composition" refers to a mixture of one or more of the compounds in specific forms or salts thereof according to the disclosure and a pharmaceutically acceptable excipient. An object of the pharmaceutical composition is to facilitate administering the compound according to the disclosure to an organism.

In some embodiments of the disclosure, the EGFR-mediated disease is selected from diseases mediated by EGFR-L858R activating mutations. In some embodiments of the disclosure, the EGFR-mediated disease is selected from diseases mediated by EGFR-T790M activating mutations. In some embodiments of the disclosure, the EGFR-mediated disease is selected from diseases mediated by double mutations of the combined EGFR-L858R and EGFR-T790M mutation. In some embodiments of the disclosure, the EGFR-mediated disease is cancer; the cancer is selected from the group consisting of ovarian cancer, cervical cancer, colorectal cancer, breast cancer, pancreatic cancer, glioma, glioblastoma, melanoma, prostate cancer, leukemia, lymphoma, non-Hodgkin's lymphoma, gastric cancer, lung cancer, hepatocellular carcinoma, gastric cancer, gastrointestinal stromal tumor, thyroid cancer, bile duct cancer, endometrial cancer, kidney cancer, anaplastic large cell lymphoma, acute myeloid leukemia, multiple myeloma, and mesothelioma; and the lung cancer may be selected from the group consisting of non-small cell lung cancer, small cell lung cancer, lung adenocarcinoma, and lung squamous cell carcinoma.

The stability of the crystal according to the disclosure may be detected by placing the crystal in a high temperature, a high humidity, or a lighting condition. 40-60° C. may be selected for the high temperature, the relative humidity of 75%-92.5% RH may be selected for the high humidity condition, and 5000 Lux may be selected for the lighting condition. The crystal stability may be evaluated by investigating a plurality of data, such as content, total content of impurities, or water content, of the sample, and comprehensively evaluating the parameters according to the properties of the product.

All reagents used in the disclosure are available on the market, and can be used without further purification. The reactions are generally carried out in an anhydrous solvent under an inert nitrogen atmosphere.

In the disclosure, the proton nuclear magnetic resonance data are recorded in a Bruker Avance III HD 500M spectrometer; the chemical shift is expressed in ppm in downfield from tetramethylsilane; and the mass spectrum is measured by Waters ACQUITY UPLC+XEVO G2 QTof. The mass spectrometer is equipped with an electrospray ionization (ESI) operated in a positive or negative mode.

The crystal of the compound represented by formula I according to the disclosure has advantages of high purity, high crystallinity, and good stability. Furthermore, the method for preparing a crystal of the compound represented by formula I according to the disclosure is simple, has inexpensive available solvents and a mild crystallization condition, and therefore is suitable for industrial production.

EXAMPLES

Figure 1:
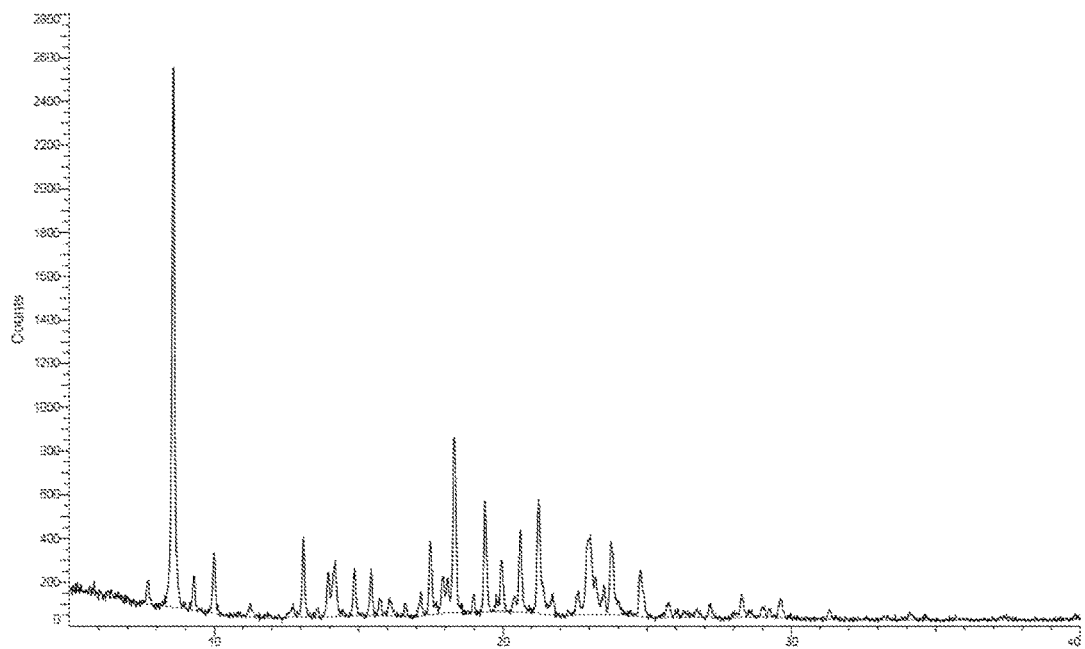
FIG. 1: an XRD pattern of a crystal A of a compound represented by formula I.
Figure 2:
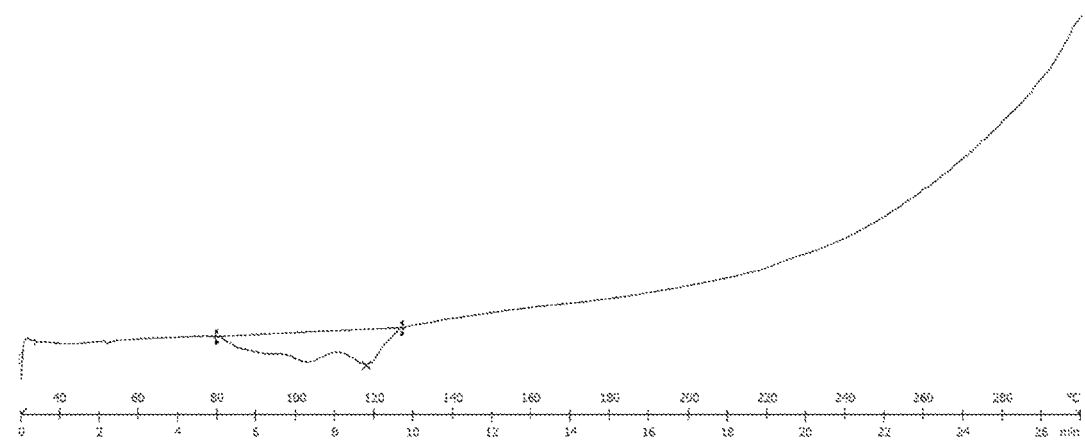
FIG. 2: a DSC thermogram of a crystal A of a compound represented by formula I.
Figure 3:
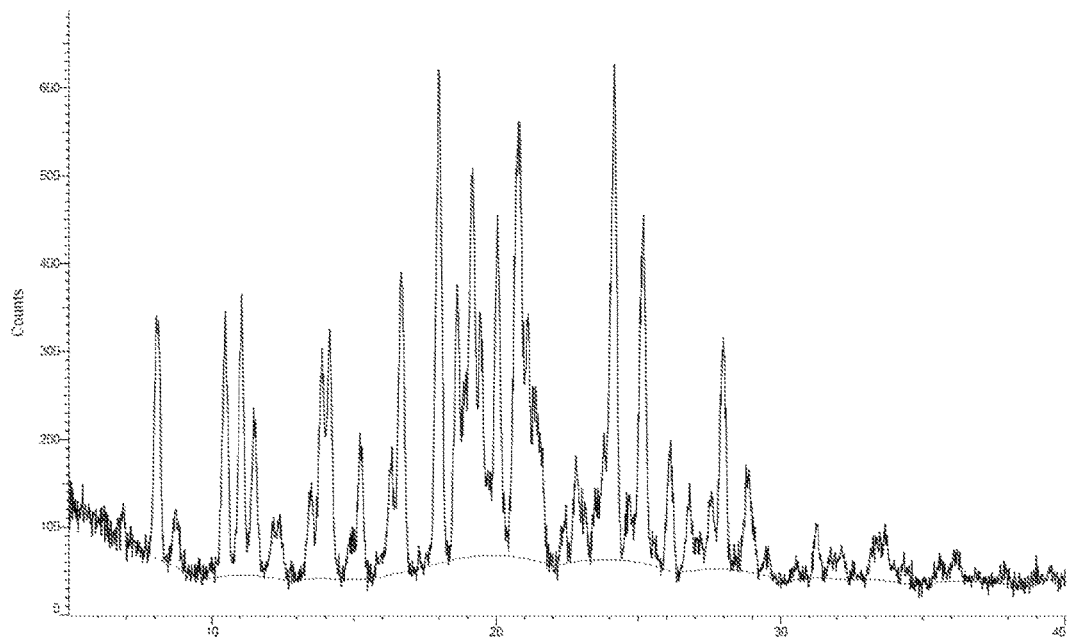
FIG. 3: an XRD pattern of a crystal B of monomethyl sulfonate of a compound represented by formula I.
Figure 4:
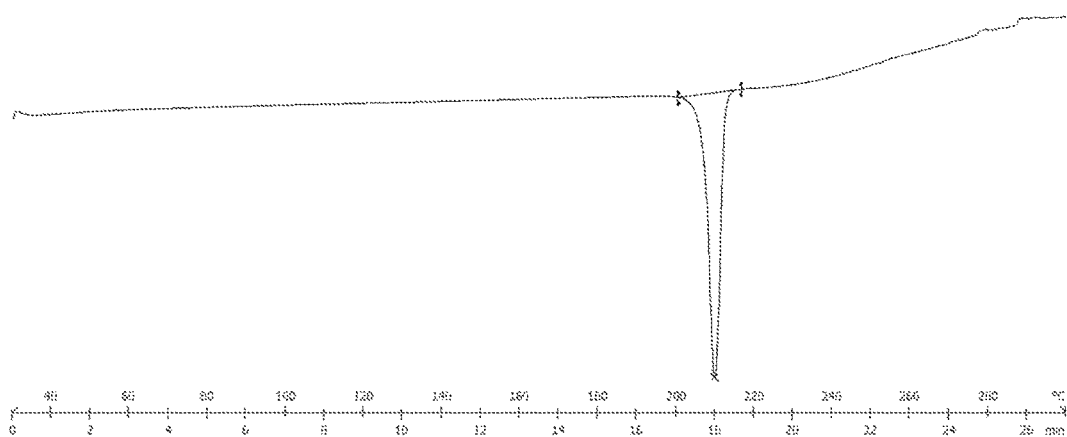
FIG. 4: a DSC thermogram of a crystal B of monomethyl sulfonate of a compound represented by formula I.
Figure 5:
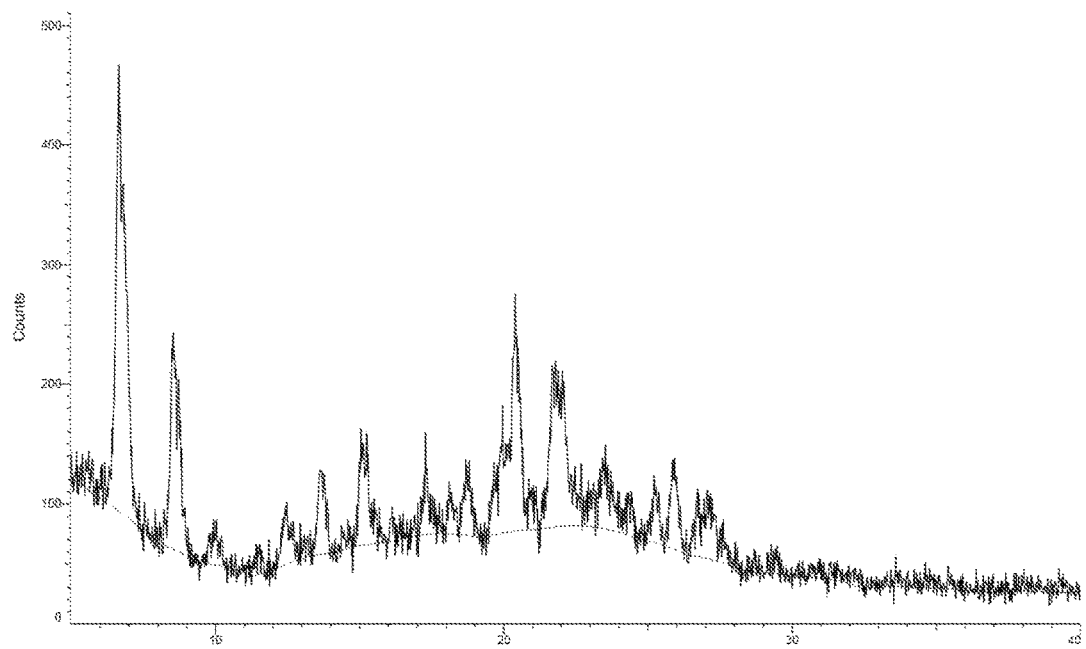
FIG. 5: an XRD pattern of a crystal C of dimethyl sulfonate of a compound represented by formula I.
Figure 6:
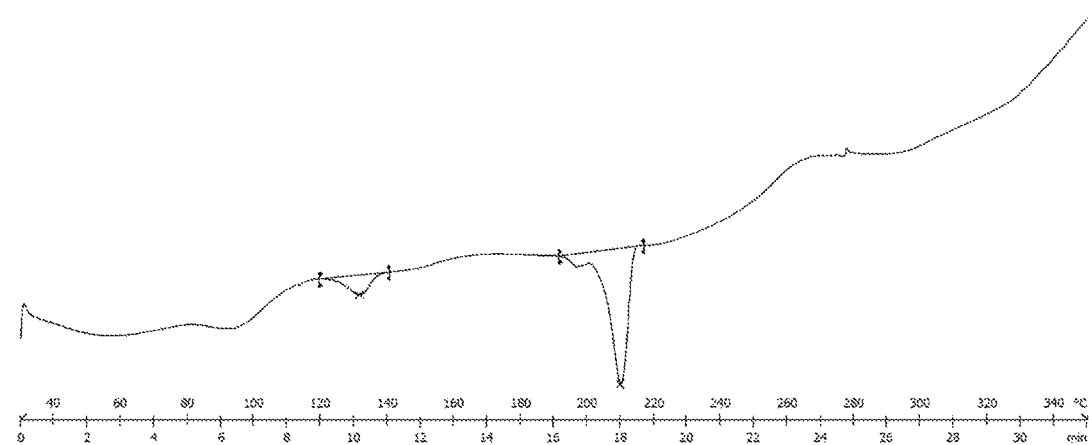
FIG. 6: a DSC thermogram of a crystal C of dimethyl sulfonate of a compound represented by formula I.
Figure 7:
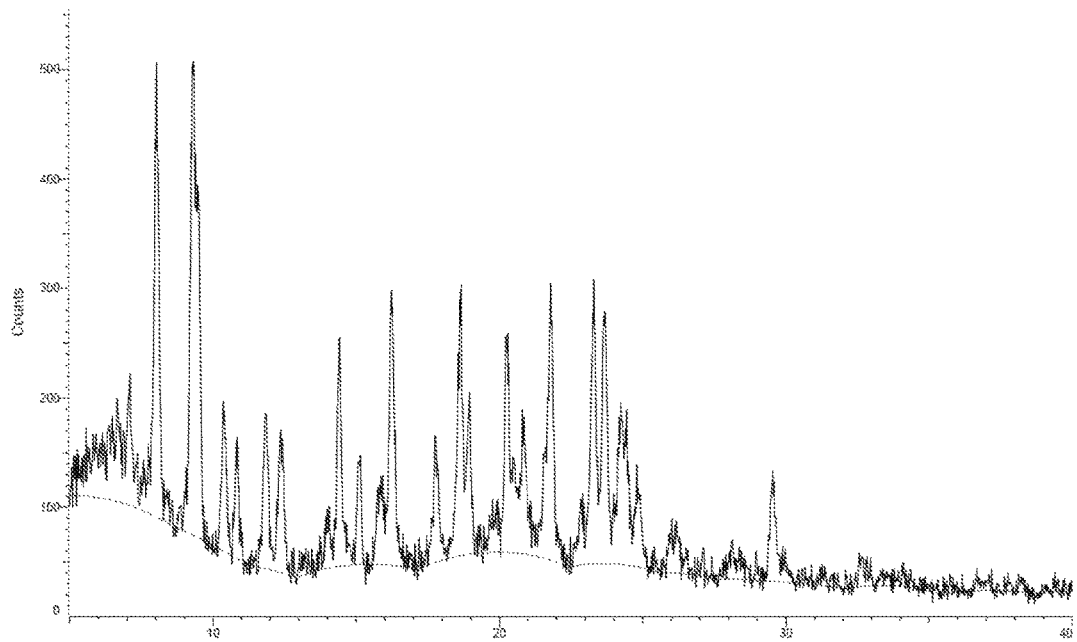
FIG. 7: an XRD pattern of a crystal D of dimethyl sulfonate of a compound represented by formula I.
Figure 8:
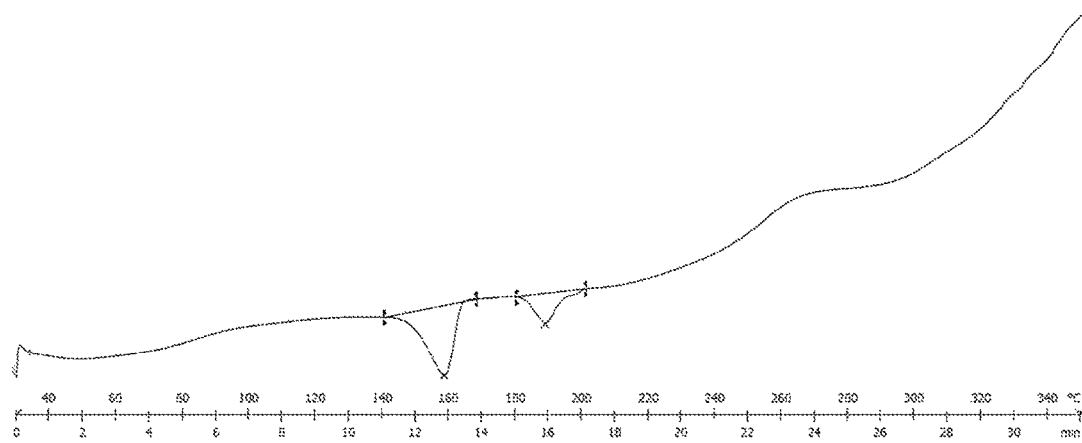
FIG. 8: a DSC thermogram of a crystal D of dimethyl sulfonate of a compound represented by formula I.
Figure 9:
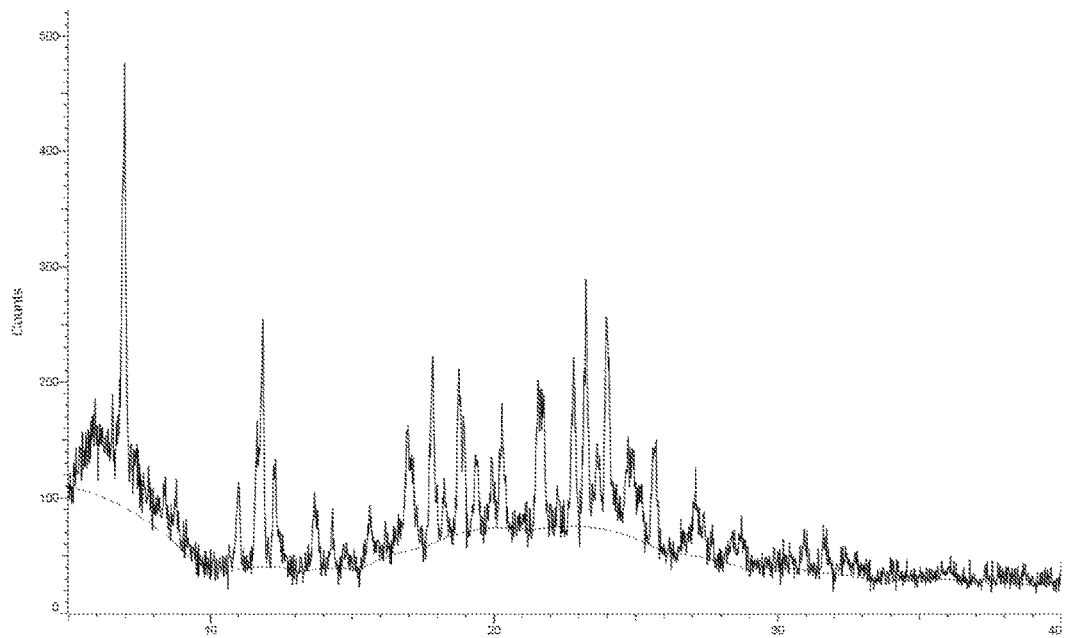
FIG. 9: an XRD pattern of a crystal E of dimethyl sulfonate of a compound represented by formula I.
Figure 10:
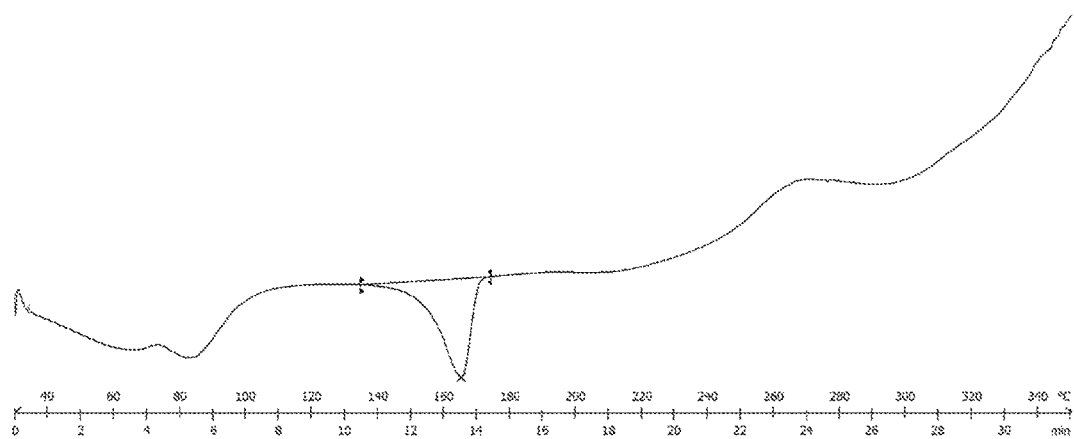
FIG. 10: a DSC thermogram of a crystal E of dimethyl sulfonate of a compound represented by formula I.
Figure 11:
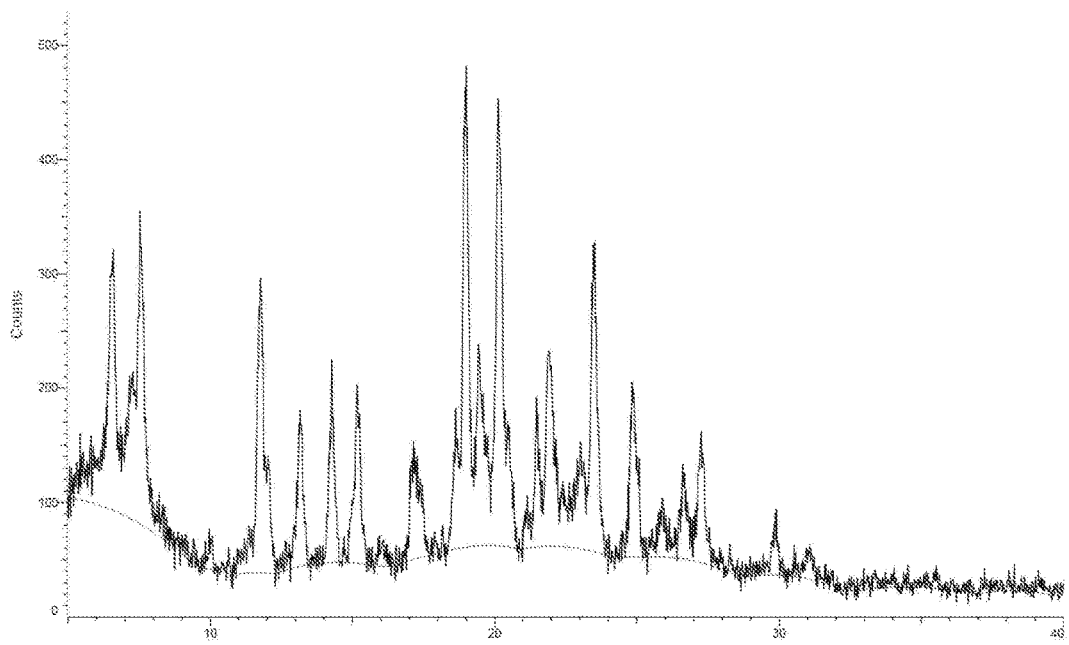
FIG. 11: an XRD pattern of a crystal F of dimethyl sulfonate of a compound represented by formula I.
Figure 12:
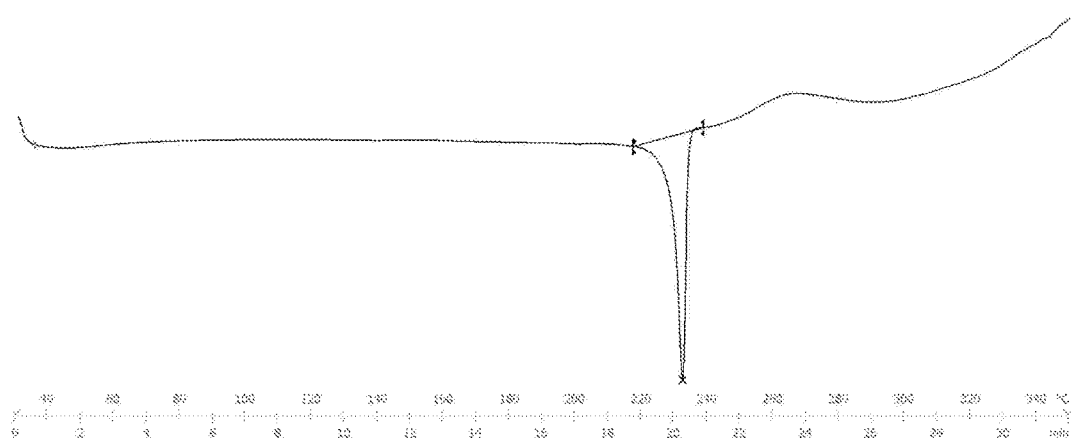
FIG. 12: a DSC thermogram of a crystal F of dimethyl sulfonate of a compound represented by formula I.
Figure 13:
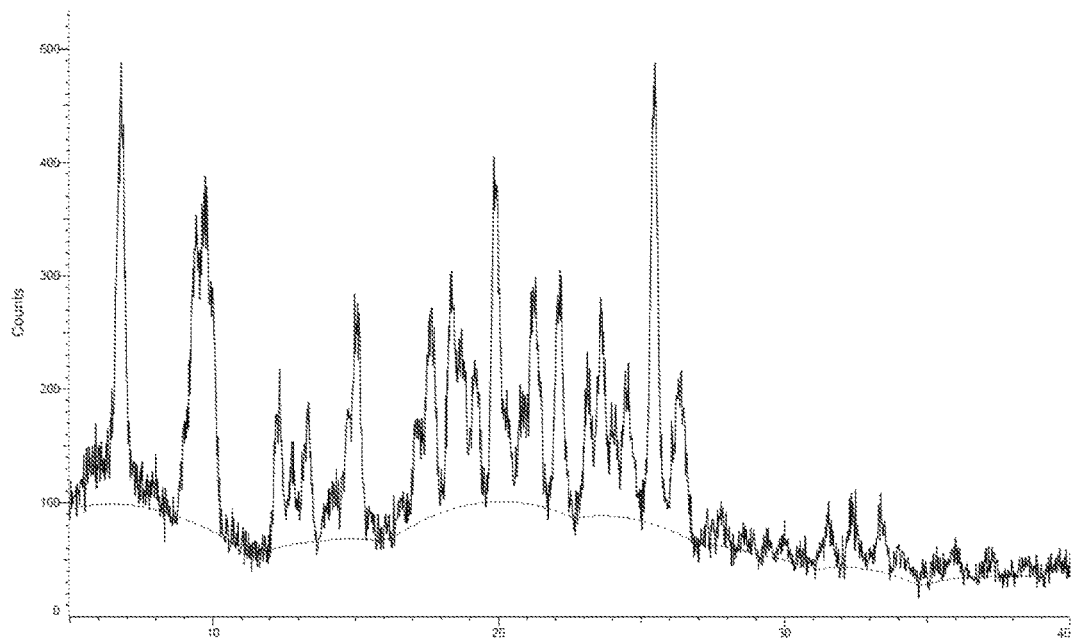
FIG. 13: an XRD pattern of a crystal G of dimethyl sulfonate of a compound represented by formula I.
Figure 14:
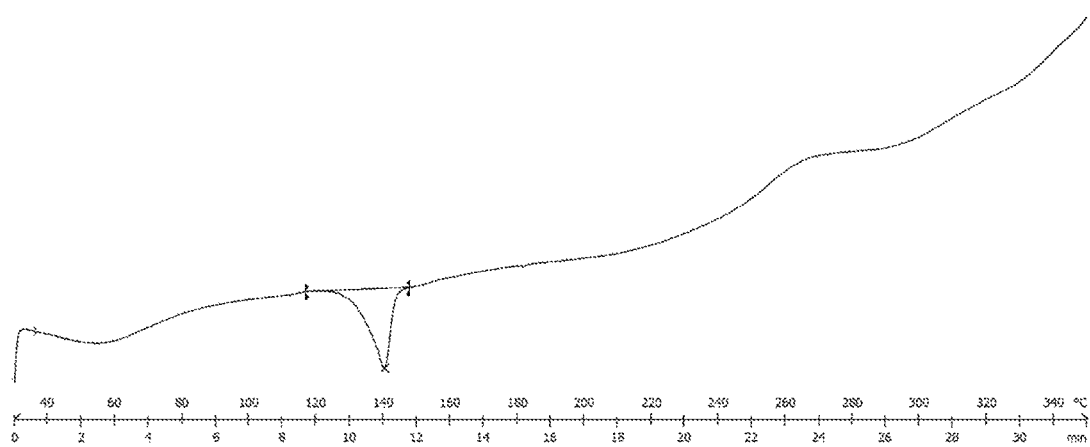
FIG. 14: a DSC thermogram of a crystal G of dimethyl sulfonate of a compound represented by formula I.

The following examples are provided only for non-limiting detailed description of the technical solution of the disclosure. They should not be construed as limiting the scope of the disclosure, but as merely illustrations and typical representatives of the present disclosure. The solvents, reagents, and starting materials used in the disclosure are chemically pure or analytically pure products available on the market.

Example 1: Amorphous Form of Compound Represented by Formula I

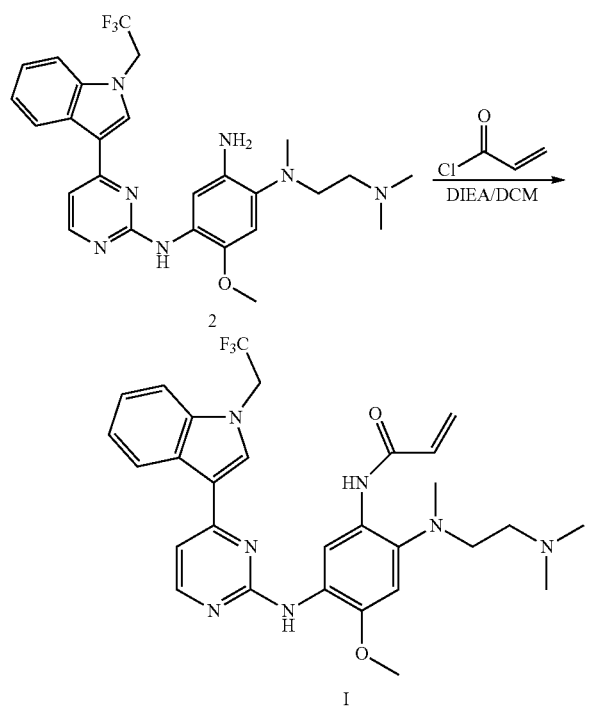

To a 1 L three-necked flask were added a compound represented by formula 2 (18.9 g, 0.037 mol), DIEA (9.6 g, 0.074 mol) and DCM (400 mL), and the mixture was magnetically stirred for dissolving. Air in the system was replaced with nitrogen, the reaction solution was cooled to −20 to −10° C., and acryloyl chloride (3.4 g, 0.037 mol) was added dropwise. Upon completion of the dropwise addition, the system was kept at −20 to −10° C. for 20 min. After the reaction was completed, water (300 mL) was added to the reaction system for stratification. The organic phase was washed with a saturated saline solution (200 ml*2), and dried over anhydrous sodium sulfate. After vacuum filtration, the filtrate was concentrated to obtain a residue, which was purified by column chromatography (DCM/MeOH=50/1 to 20/1) to yield a compound represented by formula I (10.0 g, 47.6%).

Example 2: Crystal a of Compound Represented by Formula I

The product (0.5 g) obtained in Example 1 and acetonitrile (2.5 mL) were added to a glass reaction flask, and stirred at room temperature under the protection of nitrogen. 5 min later, the solid was fully dissolved, and a solid was immediately precipitated. After stirring at room temperature for another 3 h, the content of solid increased. After filtration, the resulting solid was dried under vacuum at 45±5° C. to obtain an off-white solid, yield: 98%.

Example 3: Crystal B of Monomethyl Sulfonate of Compound Represented by Formula I Acetonitrile (2.5 mL) was added to a glass reaction flask, and stirred at room temperature under the protection of nitrogen, and then the product (0.5 g) obtained in Example 1 was added. About 5 min later, the product was fully dissolved, the reaction solution became light yellow and clear, and a solution of methanesulfonic acid (84.7 mg) in acetonitrile (0.5 mL) was immediately dropwise added to the reaction system over 2 min. About 0.5 h later, an off-white solid was precipitated. The reaction system was stirred at room temperature for another 3 h, and filtered. The resulting solid was dried under vacuum at 45±5° C. to obtain an off-white solid, yield: 90.7%.

Example 4: Crystal C of Dimethyl Sulfonate of Compound Represented by Formula I The product (0.25 g) obtained in Example 1 and acetonitrile (1.25 mL) were added to a glass reaction flask, and stirred at room temperature under the protection of nitrogen. About 5 min later, the product was fully dissolved, a solution of methanesulfonic acid (2× molar mass) in acetonitrile (0.5 mL) was immediately slowly dropwise added to the reaction system over 2 min, and the reaction solution became deep yellow and clear. The reaction system was stirred at room temperature for 15 h, a yellow solid was precipitated, and then the reaction system was filtered. The resulting solid was dried under vacuum at 45±5° C. to obtain an orange solid, yield: 44.9%.

Example 5: Crystal D of Dimethyl Sulfonate of Compound Represented by Formula I Ethyl acetate (1.5 mL) was added to a glass reaction flask, and stirred at room temperature under the protection of nitrogen, and then the product (0.25 g) obtained in Example 1 was added. After the product was fully dissolved, a solution of methanesulfonic acid (85.0 mg) in ethyl acetate (0.5 mL) was immediately added dropwise over 2 min. Upon completion of the addition, an orange yellow viscous solid was precipitated immediately, and the reaction system was stirred at room temperature for 15 h, and filtered. The resulting solid was dried under vacuum at 45±5° C. to obtain a light yellow solid, yield: 79.3%.

Example 6: Crystal E of Dimethyl Sulfonate of Compound Represented by Formula I Dichloromethane (1.5 mL) was added to a glass reaction flask, and stirred at room temperature under the protection of nitrogen, and then the product (0.25 g) obtained in Example 1 was added. After the product was fully dissolved, a solution of methanesulfonic acid (85.0 mg) in dichloromethane (0.5 mL) was immediately added dropwise over 2 min. The reaction solution became orange yellow and clear, and was stirred at room temperature for 15 h, and then a considerable amount of yellow solid was precipitated. After filtration, the resulting solid was dried under vacuum at 45±5° C. to obtain a light yellow solid, yield: 83.8%.

Example 7: Crystal F of Dimethyl Sulfonate of Compound Represented by Formula I Acetone (1.5 mL) was added to a glass reaction flask, and stirred at room temperature under the protection of nitrogen, and then the product (0.25 g) obtained in Example 1 was added. About 2 min later, the product was fully dissolved, and then a solution of methanesulfonic acid (85.0 mg) in acetone (0.5 mL) was immediately added dropwise. The reaction solution became orange yellow and clear, and was stirred at room temperature for 15 h, and then a considerable amount of yellow solid was precipitated. After filtration, the resulting solid was dried under vacuum at 45±5° C. to obtain a yellow solid, yield: 82.0%.

Example 8: Crystal G of Dimethyl Sulfonate of Compound Represented by Formula I

Dioxane (1.5 mL) was added to a glass reaction flask, and stirred at room temperature under the protection of nitrogen, and then the product (0.25 g) obtained in Example 1 was added. About 2 min later, the product was fully dissolved, and a solution of methanesulfonic acid (85.0 mg) in dioxane (0.5 mL) was immediately added dropwise over 2 min. An orange yellow viscous solid was immediately precipitated, and the reaction system was stirred at room temperature for 15 h, and filtered. The resulting solid was dried under vacuum at 45±5° C. to obtain a yellow solid, yield: 94.9%.

Test Example 1: Stability Test for Crystal of Compound Represented by Formula I, Crystal of Monomethyl Sulfonate, and Crystal of Dimethyl Sulfonate The stability of the crystal according to the disclosure was investigated under accelerated test conditions according to the *Guiding Principles for Stability Test of Crude Drugs and Pharmaceutical Preparations*. The stabilities of the crystals obtained in Examples 1-8 were tested in a light environment at 5000 Lx±500 Lx, a high temperature environment at 60° C.±2° C., and a high humidity environment at 75% RH±5% RH, respectively. Samples were taken on the 5th day, the 10th day, and the 30th day, respectively, and the appearance properties, moisture contents, and total impurities of related substances of the samples were recorded for comparison with the initial data. The comparison result shows that the crystals obtained in Examples 1-8 of the disclosure have good stability, and especially the crystals obtained in Examples 3, 6, and 7 have better stability.

What is claimed is:

1. A crystal A of a compound represented by formula I:

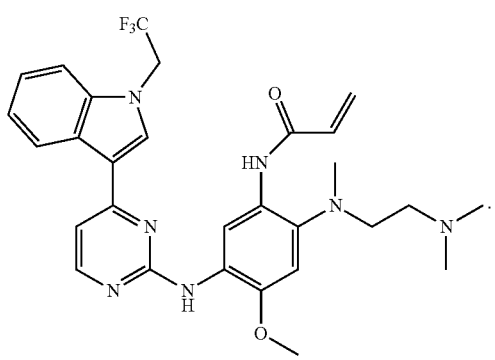

I having diffraction peaks at 2θ=8.58°, 13.10°, 18.32°, 19.39°, and 21.29°±0.2° in an X-ray diffraction pattern; typically having diffraction peaks at 2θ=8.58°, 9.98°, 13.10°, 17.53°, 18.32°, 19.39°, and 21.29°±0.2°, and more typically having diffraction peaks at 2θ=8.58°, 9.98°, 13.10°, 17.53°, 18.32°, 19.39°, 20.57°, 21.29°, 23.04°, and 23.76°±0.2°.

2. A crystal B of monomethyl sulfonate of a compound represented by formula I:

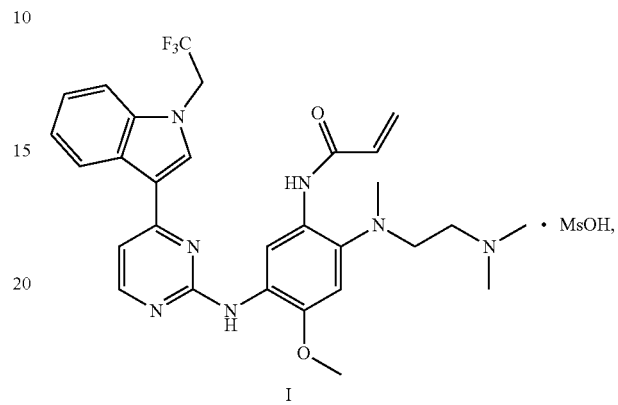

I having diffraction peaks at 2θ=8.05°, 11.08°, 14.17°, 17.98°, 19.20°, 20.78°, and 24.18°±0.2° in an X-ray diffraction pattern; typically having diffraction peaks at 2θ=8.05°, 10.46°, 11.08°, 11.48°, 14.17°, 17.98°, 19.20°, 20.78°, 24.18°, and 25.15°±0.2°; more typically having diffraction peaks at 2θ=8.05°, 10.46°, 11.08°, 11.48°, 14.17°, 16.65°, 17.98°, 18.61°, 19.20°, 20.03°, 20.78°, 24.18°, and 25.15°±0.2°; and further typically having diffraction peaks at 2θ=8.05°, 10.46°, 11.08°, 11.48°, 13.86°, 14.17°, 16.65°, 17.98°, 18.61°, 19.20°, 19.40°, 20.03°, 20.78°, 21.12°, 24.18°, 25.15°, and 27.96°±0.2°.

3. A crystal C of dimethyl sulfonate of a compound represented by formula I:

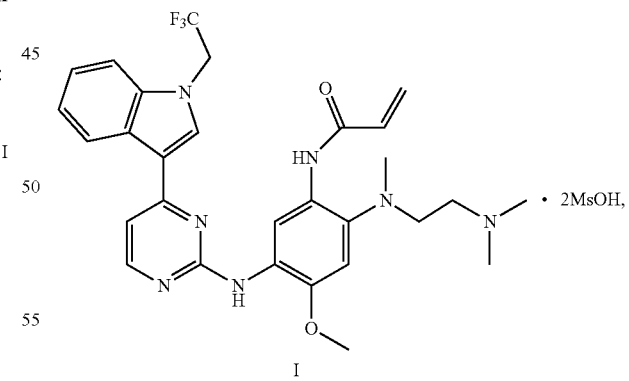

I having diffraction peaks at 2θ=6.64°, 8.48°, 17.25°, 20.40°, and 21.87°±0.2° in an X-ray diffraction pattern; typically having diffraction peaks at 2θ=6.64°, 8.48°, 13.70°, 15.16°, 17.25°, 20.07°, 20.40°, and 21.87°±0.2°; and more typically having diffraction peaks at 2θ=6.64°, 8.48°, 13.70°, 15.16°, 17.25°, 19.65°, 20.07°, 20.40°, 21.87°, 23.53°, and 25.90°±0.2°.

4. A crystal D of dimethyl sulfonate of a compound represented by formula I:

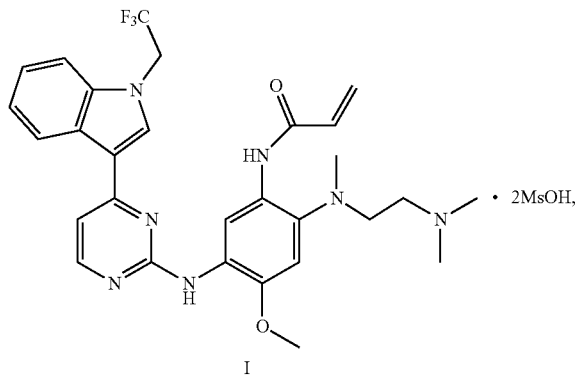

I having diffraction peaks at 2θ=8.04°, 9.35°, 14.42°, 16.23°, 18.64°, 21.83°, and 23.20°±0.2° in an X-ray diffraction pattern; typically having diffraction peaks at 2θ=8.04°, 9.35°, 11.86°, 14.42°, 16.23°, 18.64°, 20.32°, 21.83°, 23.30°, and 23.65°±0.2°; more typically having diffraction peaks at 2θ=7.12°, 8.04°, 9.35°, 11.86°, 12.37°, 14.42°, 16.23°, 18.64°, 18.98°, 20.32°, 21.83°, 23.30°, 23.65°, and 24.45°±0.2°; and further typically having diffraction peaks at 2θ=7.12°, 8.04°, 9.35°, 10.37°, 11.86°, 12.37°, 14.42°, 16.23°, 17.79°, 18.64°, 18.98°, 20.32°, 20.82°, 21.83°, 23.30°, 23.65°, 24.22°, and 24.45°±0.2°.

5. A crystal E of dimethyl sulfonate of a compound represented by formula I:

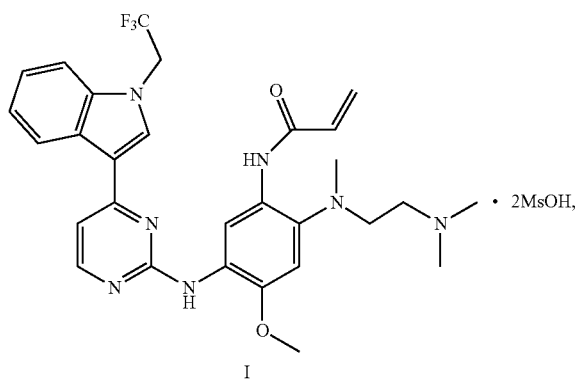

I having diffraction peaks at 2θ=6.98°, 11.85°, 17.83°, 18.76°, 20.29°, 23.26°, and 23.99°±0.2° in an X-ray diffraction pattern; typically having diffraction peaks at 2θ=6.98°, 10.98°, 11.85°, 17.00°, 17.83°, 18.76°, 20.29°, 22.84°, 23.26°, and 23.99°±0.2°; and more typically having diffraction peaks at 2θ=6.98°, 10.98°, 11.85°, 12.30°, 17.00°, 17.83°, 18.76°, 20.29°, 21.65°, 22.84°, 23.26°, 23.99°, and 25.69°±0.2°.

6. A crystal F of dimethyl sulfonate of a compound represented by formula I:

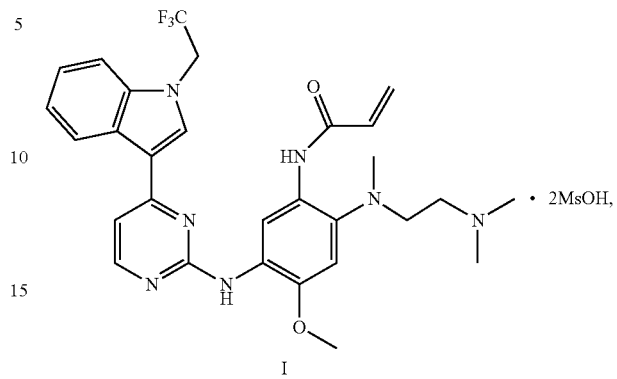

I having diffraction peaks at 2θ=6.53°, 7.52°, 11.84°, 19.02°, 19.41°, 20.16°, 23.50°±0.2° in an X-ray diffraction pattern; typically having diffraction peaks at 2θ=6.53°, 7.52°, 11.84°, 14.29°, 19.02°, 19.41°, 20.16°, 21.96°, 23.50°, 24.90°, 27.26°±0.2°; and more typically having diffraction peaks at 2θ=6.53°, 7.52°, 11.84°, 13.17°, 14.29°, 15.17°, 18.60°, 19.02°, 19.41°, 20.16°, 21.51°, 21.96°, 23.50°, 24.90°, and 27.26°±0.2°.

7. A crystal G of dimethyl sulfonate of a compound represented by formula I:

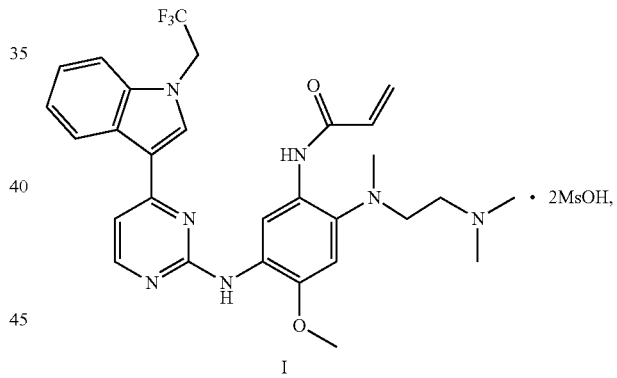

I having diffraction peaks at 2θ=6.80°, 9.71°, 15.11°, 18.35°, 19.91°, and 25.48°±0.2° in an X-ray diffraction pattern; typically having diffraction peaks at 2θ=6.80°, 9.71°, 12.32°, 15.11°, 17.64°, 18.35°, 19.91°, 21.26°, 23.60°, and 25.48°±0.2°; and more typically having diffraction peaks at 2θ=6.80°, 9.71°, 12.32°, 13.32°, 15.11°, 17.64°, 18.35°, 18.72°, 19.91°, 21.26°, 23.11°, 23.60°, 24.51°, and 25.48°±0.2°.

8. A method for treating an EGFR-mediated disease in a subject, comprising administrating to the subject a therapeutically effective amount of the crystal A of claim 1, wherein the EGFR-mediated disease is lung cancer.

9. A method for treating an EGFR-mediated disease in a subject, comprising administrating to the subject a therapeutically effective amount of the crystal B of claim 2, wherein the EGFR-mediated disease is lung cancer.

10. A method for treating an EGFR-mediated disease in a subject, comprising administrating to the subject a therapeutically effective amount of the crystal C of claim 3, wherein the EGFR-mediated disease is lung cancer.

11. A method for treating an EGFR-mediated disease in a subject, comprising administrating to the subject a therapeutically effective amount of the crystal D of claim 4, wherein the EGFR-mediated disease is lung cancer.

12. A method for treating an EGFR-mediated disease in a subject, comprising administrating to the subject a therapeutically effective amount of the crystal E of claim 5, wherein the EGFR-mediated disease is lung cancer.

13. A method for treating an EGFR-mediated disease in a subject, comprising administrating to the subject a therapeutically effective amount of the crystal F of claim 6, wherein the EGFR-mediated disease is lung cancer.

14. A method for treating an EGFR-mediated disease in a subject, comprising administrating to the subject a therapeutically effective amount of the crystal G of claim 7, wherein the EGFR-mediated disease is lung cancer.

* * * * *